(12) United States Patent
Al-Saggaf et al.

(10) Patent No.: US 11,344,248 B1
(45) Date of Patent: *May 31, 2022

(54) WEARABLE STRESS ASSESSMENT SYSTEM WITH EEG SENSORS

(71) Applicant: King Abdulaziz University, Jeddah (SA)

(72) Inventors: Ubaid M. Al-Saggaf, Jeddah (SA); Mohammed U. Alsaggaf, Jeddah (SA); Muhammad Moinuddin, Jeddah (SA); Syed Saad Azhar Ali, Seri Iskandar (MY); Syed Faraz Naqvi, Seri Iskandar (MY)

(73) Assignee: King Abdulaziz University, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/479,616

(22) Filed: Sep. 20, 2021

Related U.S. Application Data

(62) Division of application No. 17/324,796, filed on May 19, 2021, now Pat. No. 11,179,089.

(51) Int. Cl.
    *A61B 5/00*         (2006.01)
    *A61B 5/16*         (2006.01)
    (Continued)

(52) U.S. Cl.
    CPC ............ *A61B 5/374* (2021.01); *A61B 5/0006* (2013.01); *A61B 5/256* (2021.01); *A61B 5/291* (2021.01);
    (Continued)

(58) Field of Classification Search
None
See application file for complete search history.

(56) References Cited

U.S. PATENT DOCUMENTS

| 10,812,424 B1 | 10/2020 | Bommaraju |
| 11,051,748 B2 | 7/2021 | Keane |

(Continued)

FOREIGN PATENT DOCUMENTS

| CN | 110442232 A | 11/2019 |
| CN | 110515456 A | 11/2019 |
| KR | 10-2143910 | 8/2020 |

OTHER PUBLICATIONS

Ahn, et al.; A Novel Wearable EEG and ECG Recording System for Stress Assessment; Sensors 2-19, 19; 14 Pages; Apr. 28, 2019.

(Continued)

*Primary Examiner* — Etsub D Berhanu
(74) *Attorney, Agent, or Firm* — Oblon, McClelland, Maier & Neustadt, L.L.P.

(57) ABSTRACT

A method and system that includes a wearable device having a plurality of EEG sensors to detect an EEG signal in a window of a predetermined length, a bandpass filter to remove frequency bands of the EEG signal to obtain a combined signal of remaining frequency bands, and a wireless device connection for wireless transmission of information from the wearable device. The information including the EEG signal and the combined signal. A mobile device includes a communication device for receiving the transmitted information, at least one processor for processing a machine learning model. The machine learning model classifies the combined signal to obtain a classification result of mental stress or not mental stress, and a display device displays a mental stress assessment based on the EEG signal and the classification result.

1 Claim, 9 Drawing Sheets

(51) Int. Cl.
*A61B 5/374* (2021.01)
*A61B 5/291* (2021.01)
*A61B 5/256* (2021.01)

(52) U.S. Cl.
CPC ............ *A61B 5/725* (2013.01); *A61B 5/7264* (2013.01); *A61B 2560/0475* (2013.01)

(56) References Cited

U.S. PATENT DOCUMENTS

| | | |
|---|---|---|
| 2010/0145215 A1 | 6/2010 | Pradeep et al. |
| 2014/0316230 A1 | 10/2014 | Denison |
| 2020/0046244 A1 | 2/2020 | Alam |
| 2020/0107766 A1 | 4/2020 | Liu |
| 2020/0188697 A1 | 6/2020 | Kabrams |

OTHER PUBLICATIONS

Dar, et al.; CNN and LSTM-Based Emotion Charting Using Physiological Signals; Sensors 2020, 20; 26 Pages; Aug. 14, 2020.

Saeedi et al. Major depressive disorder diagnosis based on effective connectivity in EEG signals: a convolutional neural network and long short-term memory approach. Cognitive Neurodynamics (2021) 15:239-252. (Year: 2021).

Chakladar et al. EEG-based mental workload estimation using deep BLSTM-LSTM network and evolutionary algorithm. Biomedical Signal Processing and Control 60 (2020). (Year: 2020).

Li et al. Exploring temporal representations by leveraging attention-based bidirectional LSTM-RNNs for multi-modal emotion recognition. Information Processing and Management 57 (2020). (Year: 2020).

Yang et al. Emotion Recognition from Multi-Channel EEG through Parallel Convolutional Recurrent Neural Network. (Year: 2018).

WEARABLE STRESS ASSESSMENT SYSTEM WITH EEG SENSORS

CROSS-REFERENCE TO RELATED APPLICATIONS

The present application is a Divisional of U.S. application Ser. No. 17/324,796, pending, having a filing date of May 19, 2021.

BACKGROUND

Technical Field

The present disclosure is directed to a mental stress assessment system and method with machine learning provided with EEG signals.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Early diagnosis is essential to prevent severe health problems caused by mental stress. Some methods and techniques may provide a general indicator that the person is stressed or not. Most clinical professionals tend to use a questionnaire-based assessment involving the perceived stress scale, see J. E. Dise-Lewis, "The life events and coping inventory: An assessment of stress in children," Psychosom. Med., vol. 50, no. 5, pp. 484-499, 1988, doi: 10.1097/00006842-198809000-00005, the stress response inventory, see K. B. Koh, J. K. Park, C. H. Kim, and S. Cho, "Development of the Stress Response Inventory and Its Application in Clinical Practice," Psychosom. Med., vol. 63, no. 4, pp. 668-678, July 2001, doi: 10.1097/00006842-200107000-00020, and life events and coping inventory, see S. Cohen, D. A. J. Tyrrell, and A. P. Smith, "Negative Life Events, Perceived Stress, Negative Affect, and Susceptibility to the Common Cold," J. Pers. Soc. Psychol., vol. 64, no. 1, pp. 131-140, 1993, doi: 10.1037/0022-3514.64.1.131, each incorporated herein by reference in their entirety. Stress assessment by such measurement methods can be difficult, as stress is vulnerable to memory, time, atmosphere, and personal relation to an event. Moreover, under the pressure of social stigma, see S. Cohen et al., and see K. Gomathi, D. Leela, and S. Prasad, "Smart System to Recognize EEG Signal for Finding Brain Diseases Using K Means Clustering," Int. J. Adv. Comput. Res., vol. 3 (4), no. 13, pp. 1-5, 2013, each incorporated herein by reference in their entirety, a person may opt for a definitive approach and reject or avoid the assessment process. In such conditions, such clinical evaluations can be inconsistent, inaccurate, and unreliable. In addition to the traditional questionnaire methodology that uses psychological testing to diagnose mental stress, physiological responses have also been used for the same purpose. The body overcomes mental stress with the aid of different biochemicals that adjust to maintain its normal balance, see "Elevated {CSF} corticotropin-releasing factor concentrations in posttraumatic stress disorder," Am. J. Psychiatry, vol. 154, no. 5, pp. 624-629, May 1997, doi: 10.1176/ajp.154.5.624; D. G. Baker et al., "Serial CSF corticotropin-releasing hormone levels and adrenocortical activity in combat veterans with post-traumatic stress disorder," Am. J. Psychiatry, vol. 156, no. 4, pp. 585-588, 1999, each incorporated herein by reference in their entirety. Changes in the body are biological. Various approaches have been used to evaluate and associate mental stress with physiological shifts. These approaches are based on determining specific physical changes related to mental stress, such as skin activity, facial expression, blood pressure, functional near-infrared spectroscopy (fNIRS), electroencephalography (EEG), and electrocardiography (ECG).

Conventionally, clinicians use EEG as a primary modality that is low-cost, non-invasive, and has the capacity to record high-resolution temporal brain information. EEG signal assessment is carried out by specialists trained to interpret EEG rhythms to detect significant pathological variations within the brain region. See S.-H. Seo and J.-T. Lee, "Stress and EEG," in Convergence and Hybrid Information Technologies, M. Crisan, Ed. Rijeka: IntechOpen, 2010; J. F. Alonso, S. Romero, M. R. Ballester, R. M. Antonijoan, and M. A. Marianas, "Stress assessment based on {EEG} univariate features and functional connectivity measures," Physiol. Meas., vol. 36, no. 7, pp. 1351-1365, May 2015, doi: 10.1088/0967-3334/36/7/1351; A. F. Rabbi, A. Zony, P. de Leon, and R. Fazel-Rezai, "Mental workload and task engagement evaluation based on changes in electroencephalogram," Biomed. Eng. Lett., vol. 2, no. 3, pp. 139-146, September 2012, doi: 10.1007/s13534-012-0065-8, each incorporated herein by reference in their entirety. The method of EEG reading is expert-oriented but can still lead to misdiagnosis S. R. Benbadis, "Errors in EEGs and the misdiagnosis of epilepsy: Importance, causes, consequences, and proposed remedies," Epilepsy Behav., vol. 11, no. 3, pp. 257-262, 2007, doi: 10.1016/j.yebeh.2007.05.013, incorporated herein by reference in its entirety. With the lack of such experts and the ever-increasing number of people experiencing mental stress, manual EEG evaluation is inefficient and time-consuming, see K. Gomathi et al. The way out is to address the demand and pressure on domain experts by using computer-aided techniques.

Computer-aided diagnosis (CAD) systems have shown promising results when used as an initial monitoring tool. The collaboration between machines and domain experts is desired to make human lives better, see D. K. S. Desai and T. M. Girish, "A Review of Applications of Expert Systems in Medical Sciences International Science Index, International Science University, eissn: 1307-6892, World Academy of Science and Engineering Technology," 2016, incorporated herein by reference in its entirety. CAD systems using modern machine learning approaches have been successfully applied to predict post-traumatic stress disorder (PTSD) or depression through EEG signals, see I. R. Galatzer-Levy, K. I. Karstoft, A. Statnikov, and A. Y. Shalev, "Quantitative forecasting of PTSD from early trauma responses: A Machine Learning application," J. Psychiatr. Res., vol. 59, pp. 68-76, 2014, doi: 10.1016/j.jpsychires.2014.08.017; M. Sharma, P. V. Achuth, D. Deb, S. D. Puthankattil, and U. R. Acharya, "An automated diagnosis of depression using three-channel bandwidth-duration localized wavelet filter bank with EEG signals," Cogn. Syst. Res., vol. 52, pp. 508-520, 2018, doi: 10.1016/j.cogsys.2018.07.010; A. J. Rosellini, F. Dussaillant, J. R. Zubizarreta, R. C. Kessler, and S. Rose, "Predicting post-traumatic stress disorder following a natural disaster," J. Psychiatr. Res., vol. 96, pp. 15-22, 2018, doi: 10.1016/j.jpsychires.2017.09.010; F. Gonalves, D. Carneiro, and P. Novais, "Monitoring Mental Stress Through Mouse Behaviour and Decision-Making Patterns," in Advances in Intelligent Systems and Computing, Springer International Publishing, 2018, pp. 40-47, each incorporated herein by reference in their entirety. Current limitations with mental stress assessment using a machine learning approach involve the inability to perfor a mental stress assessment in real-time. The core of machine learning approaches includes supervised feature extraction and selection; such a process is expert-driven and sensitive. The involvement of humans and its sensitive nature over the learning exposes it to various vulnerabilities that can affect the outcome of the model. Conventionally, experts tend to extract multiple features to achieve better performance and convergence for the learning algorithm, see M. Sharma et al.; X. Hou, Y. Liu, O. Sourina, Y. R. E. Tan, L. Wang, and W. Mueller-Wittig, "EEG Based Stress Monitoring," 2015 *IEEE Int. Conf. Syst. Man, Cybern.*, vol. 00, no. c, pp. 3110-3115, 2015, doi: 10.1109/SMC.2015.540; A. R. Subhani, A. S. Malik, N. Kamil, and M. N. M. Saad, "Difference in brain dynamics during arithmetic task performed in stress and control conditions," *IECBES 2016-IEEE-EMBS Conf. Biomed. Eng. Sci.*, no. 1, pp. 695-698, 2016, doi: 10.1109/IECBES.2016.7843539; L. Xia, A. S. Malik, and A. R. Subhani, "A physiological signal-based method for early mental-stress detection," Biomed. *Signal Process. Control*, vol. 46, no. January 2019, pp. 18-32, 2018, doi: 10.1016/j.bspc.2018.06.004, each incorporated herein by reference in their entirety. Even if the features that provide better results are carefully extracted, that system would not be compatible with a real-time system. To make a machine learning stress assessment system that is able to provide high accuracy in a minimum time period, see S. F. Naqvi et al., "Real-Time Stress Assessment Using Sliding Window Based Convolutional Neural Network," *Sensors*, vol. 20, no. 16, p. 4400, August 2020, doi: 10.3390/s20164400, incorporated herein by reference in its entirety, the time consumption to perform the feature extraction has to be reduced. Several techniques can reduce time consumption involved with the feature extraction. One approach may be to extract a single most efficient feature that could perform better than multiple features. The techniques that may be used for the stated challenge of improving efficiency may involve considerations in connectivity, and deep learning.

In literature, stress assessment has been performed using EEG signals while using conventional machine learning techniques, see J. W. Ahn, Y. Ku, and H. C. Kim, "A Novel Wearable {EEG} and {ECG} Recording System for Stress Assessment," *Sensors*, vol. 19, no. 9, p. 1991, April 2019, doi: 10.3390/s19091991; Vanitha V and P. Krishnan, "Real time stress detection system based on EEG signals." Accessed: Jan. 24, 2020. Available: www.biomedres.info; J. Minguillon, E. Perez, M. A. Lopez-Gordo, F. Pelayo, and M. J. Sanchez-Carrion, "Portable system for real-time detection of stress level," *Sensors (Switzerland)*, vol. 18, no. 8, August 2018, doi: 10.3390/s18082504, each incorporated herein by reference in their entirety. Still, there is no reporting of the time period in which the system can perform the whole process. Besides using EEG signals, stress assessment has also been performed with ECG signals with convolutional neural networks (CNN) as a classifier. Still, it uses 10s of signal batch, see J. He, K. Li, X. Liao, P. Zhang, and N. Jiang, "Real-Time Detection of Acute Cognitive Stress Using a Convolutional Neural Network From Electrocardiographic Signal," *IEEE Access*, vol. 7, pp. 42710-42717, 2019, incorporated herein by reference in its entirety, which means that the subject has to wait for 10s of recording for each classification result.

The conventional modern techniques involve features such as coherence, asymmetry, ratios, see Y. Hafeez et al., "Investigating Neurofeedback Protocols for Stress Mitigation: A Comparative Analysis of Different Stimulus Contents," *IEEE Access*, vol. 7, pp. 141021-141035, 2019, doi: 10.1109/ACCESS.2019.2944202, incorporated herein by reference in its entirety, but apart from these features, the literature contains methods that use connections among the signals or regions to analyze them and extract signification information that can be able to provide distinguishable characteristics, see F. Al-Shargie, T. B. Tang, and M. Kiguchi, "Assessment of mental stress effects on prefrontal cortical activities using canonical correlation analysis: an {fNIRS}-{EEG} study," *Biomed. Opt. Express*, vol. 8, no. 5, p. 2583, April 2017, doi: 10.1364/boe.8.002583; J. D. Bonita et al., "Time domain measures of inter-channel {EEG} correlations: a comparison of linear, nonparametric and nonlinear measures," *Cogn. Neurodyn.*, vol. 8, no. 1, pp. 1-15, September 2013, doi: 10.1007/s11571-013-9267-8, each incorporated herein by reference in their entirety. Deep learning approaches are also popular approaches, and involve CNNs and long short-term memory (LSTMs). CNNs tend to extract spatial information while LSTMs extract significant features from data that possess temporal information. For example, Salma Alhagry et al. used LSTM for the identification of emotions with EEG signals; see S. Alhagry, A. Aly, and R. A., "Emotion Recognition based on {EEG} using {LSTM} Recurrent Neural Network," *Int. J. Adv. Comput. Sci. Appl.*, vol. 8, no. 10, 2017, doi: 10.14569/ijacsa.2017.081046, incorporated herein by reference in its entirety. Erik Bresch et. alproposed sleep stage classification through EEG signals using LSTM by utilizing a single channel; E. Bresch, U. Groekathfer, and G. Garcia-Molina, "Recurrent Deep Neural Networks for Real-Time Sleep Stage Classification From Single Channel EEG," *Front. Comput. Neurosci.*, vol. 12, p. 85, 2018, doi: 10.3389/fncom.2018.00085, incorporated herein by reference in its entirety. Yasin Acikmese et al. uses LSTM to classify mental stress levels but can only achieve a maximum accuracy of 62.83%; Y. Acikmese and S. E. Alptekin, "Prediction of stress levels with {LSTM} and passive mobile sensors," *Procedia Comput. Sci.*, vol. 159, pp. 658-667, 2019, doi: 10.1016/j.procs.2019.09.221, incorporated herein by reference in its entirety. P. Wang et al. describes work on motor imagery and its classification with LSTM and states that LSTMs can be used for brain-computer interfacing (BCI); P. Wang, A. Jiang, X. Liu, J. Shang, and L. Zhang, "LSTM-Based EEG Classification in Motor Imagery Tasks," *IEEE Trans. Neural Syst. Rehabil. Eng.*, vol. 26, no. 11, pp. 2086-2095, 2018, incorporated herein by reference in its entirety. P. Wang et al. also reported that models with fewer parameters could be successfully used in real-time applications because smaller models will perform in less time, therefore making them suitable for BCI real-time application.

Conventionally, a mental stress assessment is performed by domain experts by evaluating the brain's activities. There are many modalities by which mental stress can be assessed but EEG is a non-invasive technique with a high temporal property. Evaluating such EEG signals requires domain knowledge and experience, but mental stress can still be misdiagnosed due to the subjective nature of assessment. If mental stress is not diagnosed in early-stage and correctly treated, the condition can progress towards depression, anxiety, and in some situations, suicide attempts. CAD (computer-aided diagnosis) has been developed to assist domain experts but is sensitive to features that are influenced by experts. The selection of features, in turn, dramatically affects the performance of the learning model.

Due to the nature of both approaches, real-time assessment is difficult and sometimes impossible to achieve. The incapability of such a techniques to process data in real-time makes it difficult to identify actual changes in the brain caused by mental stress. In addition, real-time assessment is difficult for domain experts as well. Therefore, a system is needed that can extract the most significant features related to mental stress in real-time, especially using wearable devices. The system should also perform mental stress assessment in real-time with high accuracy and generalization so that its implementation can be possible for all participants or patients.

Accordingly, it is one object of the present disclosure to provide methods and systems for performing mental stress assessment in real time with high accuracy for a wide range of participants. It is another object to perform the mental stress assessment using a wearable device and display results of the assessment on a display device.

SUMMARY

In an aspect, a method of real-time mental stress assessment, can include acquiring, by EEG sensors, an EEG signal; obtaining alpha, beta, and theta frequency bands from the EEG signal using a band-pass filter; performing, by processing circuitry, a Long Short Term Memory (LSTM) machine learning model to extract features of the frequency bands and classify the frequency bands to obtain a classification result of mental stress or no mental stress, wherein the extracted features are extracted in a first bidirectional LSTM layer of the model and the classification is performed in a second bidirectional LSTM layer of the model; and wirelessly transmitting the EEG signal and the classification result.

In another method, a system can include a wearable device having a plurality of EEG sensors to detect an EEG signal in a fixed-length window of a predetermined length, a bandpass filter to remove frequency bands of the EEG signal leaving a combined signal of remaining frequency bands, and a microcontroller for processing a machine learning model. The machine learning model classifies the combined signal to obtain a classification result of mental stress or not mental stress. A wireless device connection for wireless transmission of information from the wearable device, the information including the EEG signal and the classification result from the machine learning model. A display device displaying a mental stress assessment based on the EEG signal and the classification result.

In another aspect, a system, can include a wearable device having a plurality of EEG sensors to detect an EEG signal in a window of a predetermined length, a bandpass filter to remove frequency bands of the EEG signal to obtain a combined signal of remaining frequency bands, and a wireless device connection for wireless transmission of information from the wearable device, the information including the EEG signal and the combined signal. A mobile device includes a communication device for receiving the transmitted information, at least one processor for processing a machine learning model, wherein the machine learning model classifies the combined signal to obtain a classification result of mental stress or not mental stress, and a display device displaying a mental stress assessment based on the EEG signal and the classification result.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
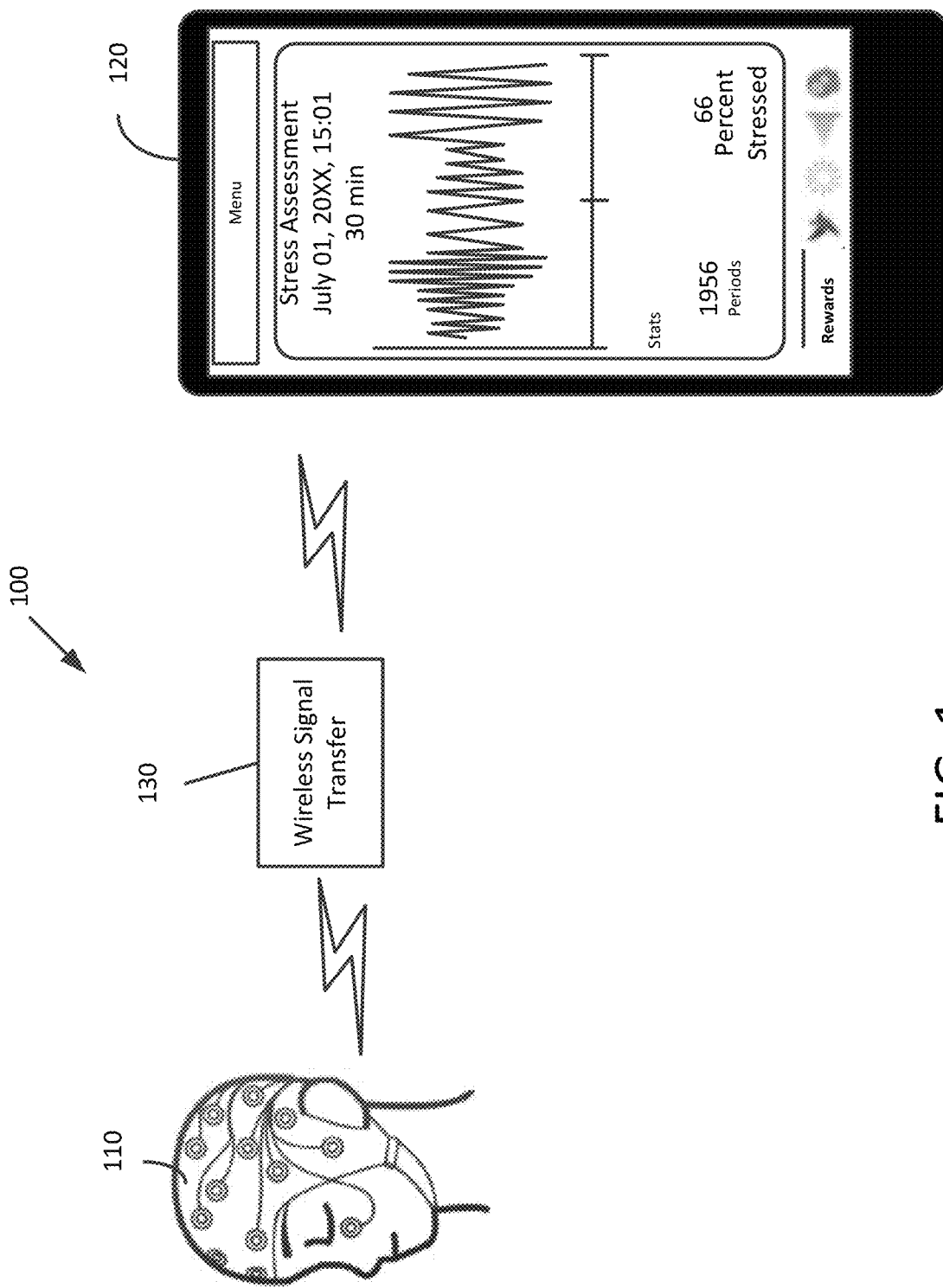
FIG. 1 is a schematic diagram of a system for mental stress assessment, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of this disclosure are directed to a system, device, and method for performing mental stress assessment in real-time with high accuracy and generalization. The system, device, and method can extract the most significant features related to mental stress in real-time, where the features are extracted from signals that are obtained using wearable devices.

In order to achieve real-time, time-efficient, and accurate mental stress assessment using raw EEG data, the method uses a Deep Learning approach as a basis. Deep learning has been typically used for image classification and anomaly detection but is still nascent when it comes to such applications with real-time signals. Among several deep learning algorithms, LSTM (Long Short-Term Memory) has been used with streaming signal data. LSTM has been successfully used for speech recognition, anomaly detection in financial trends, and many sensors-oriented problems involving temporal characteristics. In the present disclosure, LSTM may perform feature extraction automatically and is configured to reduce the overall feature extraction time. LSTM units are configured to extract the most significant features, which can solve the problem of inefficient feature extraction for conventional classification while conserving the temporal association among the data. The disclosed configuration of LSTM resolves issues with the use of machine learning or conventional clinical stress assessment.

Another issue with conventional approaches for mental stress assessment is the use of batch data for assessment. When batch data is used with conventional machine learning approaches, it is evident that such a system cannot perform as a real-time system. In order to assess batch size data, the conventional systems consume a lot of time, and for recording such large data, the participant must wait for that duration of time. Such conditions do not comply with the requirements of real-time systems. In disclosed embodiments, smaller size data or fixed-length windows can be used to perform classification in real-time. The use of smal windows also provides high resolution of the data, which is one of the empirical properties because it allows extracting significant features that are not biased or affected by other factors.

In one or more embodiments, feature extraction has been replaced by spatial or temporal extraction of features and feature selection is performed by pooling layers. The embodiments are based on deep learning approaches and use fully connected layers for final learning, and achieves generalization using activation functions and normalizing layers.

FIG. 1 is a schematic diagram of a system for mental stress assessment, according to certain embodiments. The system 100 may include a headset 110 in wireless communication with a stress assessment mobile application 120 (App). The headset 110 may be used to obtain EEG signals from the person wearing the headset 110. The wireless communication 130 may involve a direct communication link, such as Bluetooth, or Bluetooth Low Energy (BLE), or may be performed over a wireless communication network, such as WiFi. The wireless communication 130 may be used to transmit the EEG signals to the stress assessment App 120. The App can display the following results:

A graph or other visualization of sensed EEG bands related to mental stress;

Results of mental stress assessment in terms of, for example, 'Stressed' and 'Not Stressed";

Duration in terms of" % of the session time where the subject was in stress.

Figure 2:
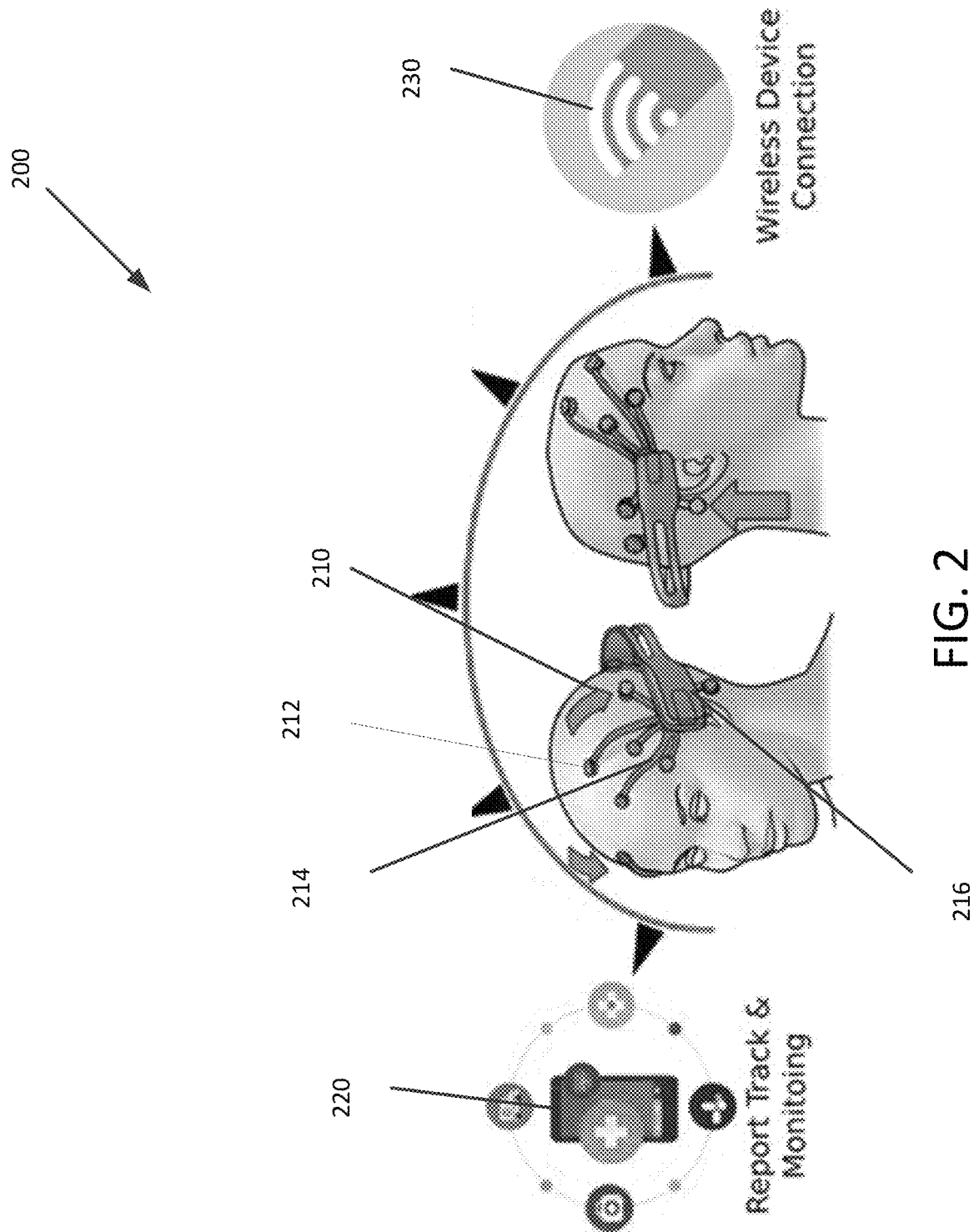
FIG. 2 is a non-limiting example of a wearable device, according to certain embodiments.

FIG. 2 is diagram non-limiting example of a wearable device having EEG sensor electrodes, according to certain embodiments. EEG is an electrophysiological monitoring method to record electrical activity on the scalp that has been shown to represent the macroscopic activity of the surface layer of the brain underneath. It is typically non-invasive, with the electrodes placed along the scalp.

EEG systems, such as wearable EEG device 210, uses electrodes 212, each of which is attached to an individual wire 214. In some embodiments, the wearable EEG device 210 may include a cap or net into which electrodes are embedded. In most clinical applications, 19 recording electrodes (plus ground and system reference) are used. A smaller number of electrodes are typically used when recording EEG from neonates. Additional electrodes can be added to the standard set-up when a clinical or research application demands increased spatial resolution for a particular area of the brain. High-density arrays (typically via cap or net) can contain up to 256 electrodes more-or-less evenly spaced around the scalp.

A wearable EEG device 210 may have sensor electrodes 212 that range from flexible electrode arrangement to rigid electrode arrangement. The electrodes 212 may be thin wired elements that can be flexibly arranged on the scalp, and mounted to the scalp via adhesive, or may be rigid wired structures that substantially stay in a fixed arrangement. In a rigid wired structure, the electrodes 212 may form a tree-like arrangement that spreads out over an area of the scalp.

In some embodiments, the wearable EEG device 210 may include one or more support members, for example a rod support member made of metal or plastic, that carries one or more wires 214 to a position of the scalp, where one or more electrodes 212 extend from an end of the support member. The wearable EEG device 210 may be a headband-type that includes a main C-shaped or oval-shaped support member that in itself contains the electrodes 212. The electrodes 212 may protrude from a surface of the support member, or may be mounted to a surface of the support member. The wearable EEG device 210 may include additional support members having ends that connect to the main support member. The additional support members may be semicircular bands that loop over the scalp so that electrodes 212 may be positioned at other areas of the scalp.

Sensor electrodes 212 may be in the shape of a cup, disc or needle. Sensor electrodes 212 may be wet or dry, in which wet electrodes 212 (e.g., felt pads) require application of a saline solution. EEG sensor electrodes 212 may obtain signals over one or more channels.

The wearable EEG device 210 may include other types of sensors, such as motion sensors (e.g. an inertial measurement unit (IMU)) to measure head movement, and temperature sensors. In addition, the system for mental stress assessment 100 may obtain optional sensor data from other sensors for an individual, such as a blood pressure measurement device, a heart rate detection device, a blood sugar monitoring probe, a blood oxygen level measurement device, to name a few. Such other sensor data may be used to determine the individual's physical condition during monitoring by the wearable EEG device 210.

In some embodiments the wearable device includes one or more first temperature probes, preferably having at least one first temperature probe proximal to each sensor electrode 212. The first temperature probes measure the surface temperature of the skin of an individual wearing the wearable device. The temperature probes are connected to the harness assembly 216 to permit transmission of temperature data together with information obtained from the sensor electrodes 212.

One or more second temperature probes may be included. The second temperature probe is not in direct contact with the skin and is preferably mounted on harness 216 such that it is spaced from the scalp and skin surface of an individual wearing the wearable device. Like the first temperature probe, the second temperature probe provides temperature data that may be transmitted by the harness.

The temperature data obtained from the first and second temperature probes can be used for purposes of calibrating the wearable device. In preferable embodiments, the temperature probes and/or differentials of temperature between the first temperature probe and second temperature probe are used as a basis for determining whether the individual wearing the wearable device is under environmental or psychological stress. For example, a temperature differential between first temperature probes may indicate that the individual is under psychological stress. The second temperature probe, alone or in combination with first temperature probes, can identify environmental stress situations, such as hot or cold environments. Comparison of temperature data from the first and second temperature probes also provides a means for identifying risk factors such as hypothermia and heat stroke.

The wearable EEG device 210 may include a harness assembly 216. The harness assembly may contain a communications device, an amplifier, an analog-to-digital converter, and a band-pass filter. Each electrode may be connected to one input of a differential amplifier (one amplifier per pair of electrodes); a common system reference electrode is connected to the other input of each differential amplifier. These amplifiers amplify the voltage between the active electrode and the reference (typically 1,000-100,000 times, or 60-100 dB of voltage gain). In analog EEG, the signal is then filtered, and the analog EEG signal is output. Most EEG systems are digital. In digital EEG, the amplified signal is digitized via an analog-to-digital converter, after being passed through an anti-aliasing filter. Analog-to-digital sampling typically occurs at 256-512 Hz in clinical scalp EEG; sampling rates of up to 20 kHz are used in some research applications. Digital EEG systems typically have a sampling rate of 256 Hz, and may have 12, 15, or 24 bit resolution.

The communications device may include a module for low energy short range communication, such as Bluetooth or BLE. The communication device may include a module for wireless communication, such as WiFi. The module for low energy short range communication may be used for communication with a mobile device 220. The module for wireless communication may be used for communication with a wireless device connection 230.

Figure 3:
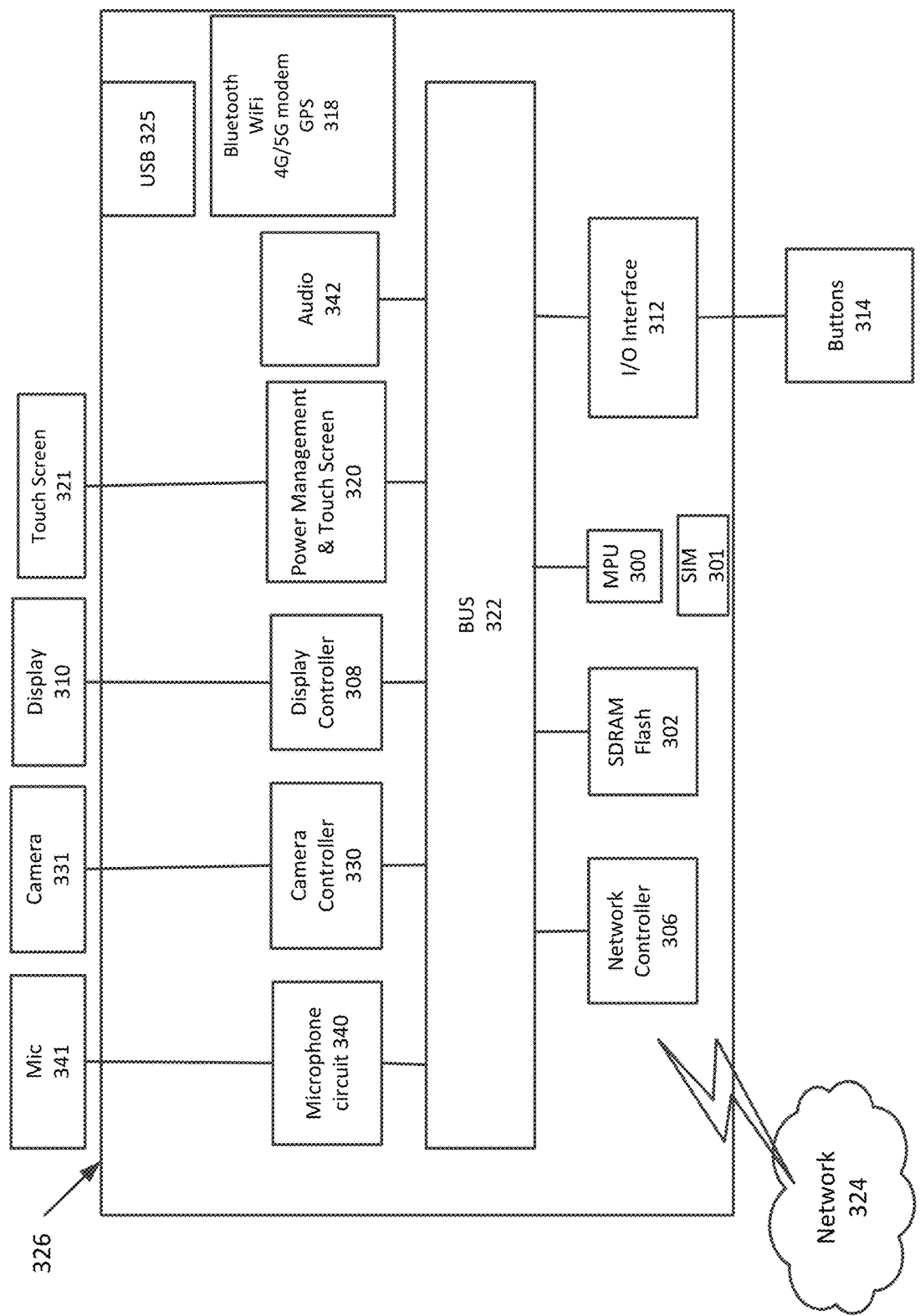
FIG. 3 is a block diagram of a non-limiting example of a mobile device, according to certain embodiments.

FIG. 3 is a block diagram of a non-limiting example of a mobile device, according to certain embodiments.

In one implementation, the functions and processes of the mobile device 220 may be implemented by one or more respective processing circuits 326. A processing circuit includes a programmed processor as a processor includes circuitry. A processing circuit may also include devices such as an application specific integrated circuit (ASIC) and conventional circuit components arranged to perform the recited functions. Note that circuitry refers to a circuit or system of circuits. Herein, the circuitry may be in one computer system or may be distributed throughout a network of computer systems.

Next, a hardware description of the processing circuit 326 according to exemplary embodiments is described with reference to FIG. 3. In FIG. 3, the processing circuit 326 includes a Mobile Processing Unit (MPU) 300 which performs the processes described herein. The process data and instructions may be stored in memory 302. These processes and instructions may also be stored on a portable storage medium or may be stored remotely. The processing circuit 326 may have a replaceable Subscriber Identity Module (SIM) 301 that contains information that is unique to the network service of the mobile device 130.

Further, the advancements are not limited by the form of the computer-readable media on which the instructions of the inventive process are stored. For example, the instructions may be stored in FLASH memory, Secure Digital Random Access Memory (SDRAM), Random Access Memory (RAM), Read Only Memory (ROM), Programmable Read-Only Memory (PROM), Erasable Programmable Read-Only Memory (EPROM), Electrically Erasable Programmable Read Only Memory (EEPROM), solid-state hard disk or any other information processing device with which the processing circuit 326 communicates, such as a server or computer.

Further, the advancements may be provided as a utility application, background daemon, or component of an operating system, or combination thereof, executing in conjunction with MPU 300 and a mobile operating system such as Android, Microsoft® Windows® 10 Mobile, Apple iOS® and other systems known to those skilled in the art.

In order to achieve the processing circuit 326, the hardware elements may be realized by various circuitry elements, known to those skilled in the art. For example, MPU 300 may be a Qualcomm mobile processor, a Nvidia mobile processor, a Atom® processor from Intel Corporation of America, a Samsung mobile processor, or a Apple A7 mobile processor, or may be other processor types that would be recognized by one of ordinary skill in the art. Alternatively, the MPU 300 may be implemented on an Field-Programmable Gate Array (FPGA), Application Specific Integrated Circuit (ASIC), Programmable Logic Device (PLD) or using discrete logic circuits, as one of ordinary skill in the art would recognize. Further, MPU 300 may be implemented as multiple processors cooperatively working in parallel to perform the instructions of the inventive processes described above.

The processing circuit 326 in FIG. 3 also includes a network controller 306, such as an Intel Ethernet PRO network interface card from Intel Corporation of America, for interfacing with network 324. As can be appreciated, the network 324 can be a public network, such as the Internet, or a private network such as LAN or WAN network, or any combination thereof and can also include PSTN or ISDN sub-networks. The network 324 can also be wired, such as an Ethernet network. The processing circuit may include various types of communications processors for wireless communications including 3G, 4G and 5G wireless modems, WiFi®, Bluetooth®, GPS, or any other wireless form of communication that is known.

The processing circuit 326 includes a Universal Serial Bus (USB) controller 325 which may be managed by the MPU 300.

The processing circuit 326 further includes a display controller 308, such as a NVIDIA® GeForce® GTX or Quadro® graphics adaptor from NVIDIA Corporation of America for interfacing with display 310. An I/O interface 312 interfaces with buttons 314, such as for volume control. In addition to the I/O interface 312 and the display 310, the processing circuit 326 may further include a microphone 341 and one or more cameras 331. The microphone 341 may have associated circuitry 340 for processing the sound into digital signals. Similarly, the camera 331 may include a camera controller 330 for controlling image capture operation of the camera 331. In an exemplary aspect, the camera 331 may include a Charge Coupled Device (CCD). The processing circuit 326 may include an audio circuit 342 for generating sound output signals, and may include an optional sound output port.

The power management and touch screen controller 320 manages power used by the processing circuit 326 and touch control. The communication bus 322, which may be an Industry Standard Architecture (ISA), Extended Industry Standard Architecture (EISA), Video Electronics Standards Association (VESA), Peripheral Component Interface (PCI), or similar, for interconnecting all of the components of the processing circuit 326. A description of the general features and functionality of the display 310, buttons 314, as well as the display controller 308, power management controller 320, network controller 306, and I/O interface 312 is omitted herein for brevity as these features are known.

Figure 4:
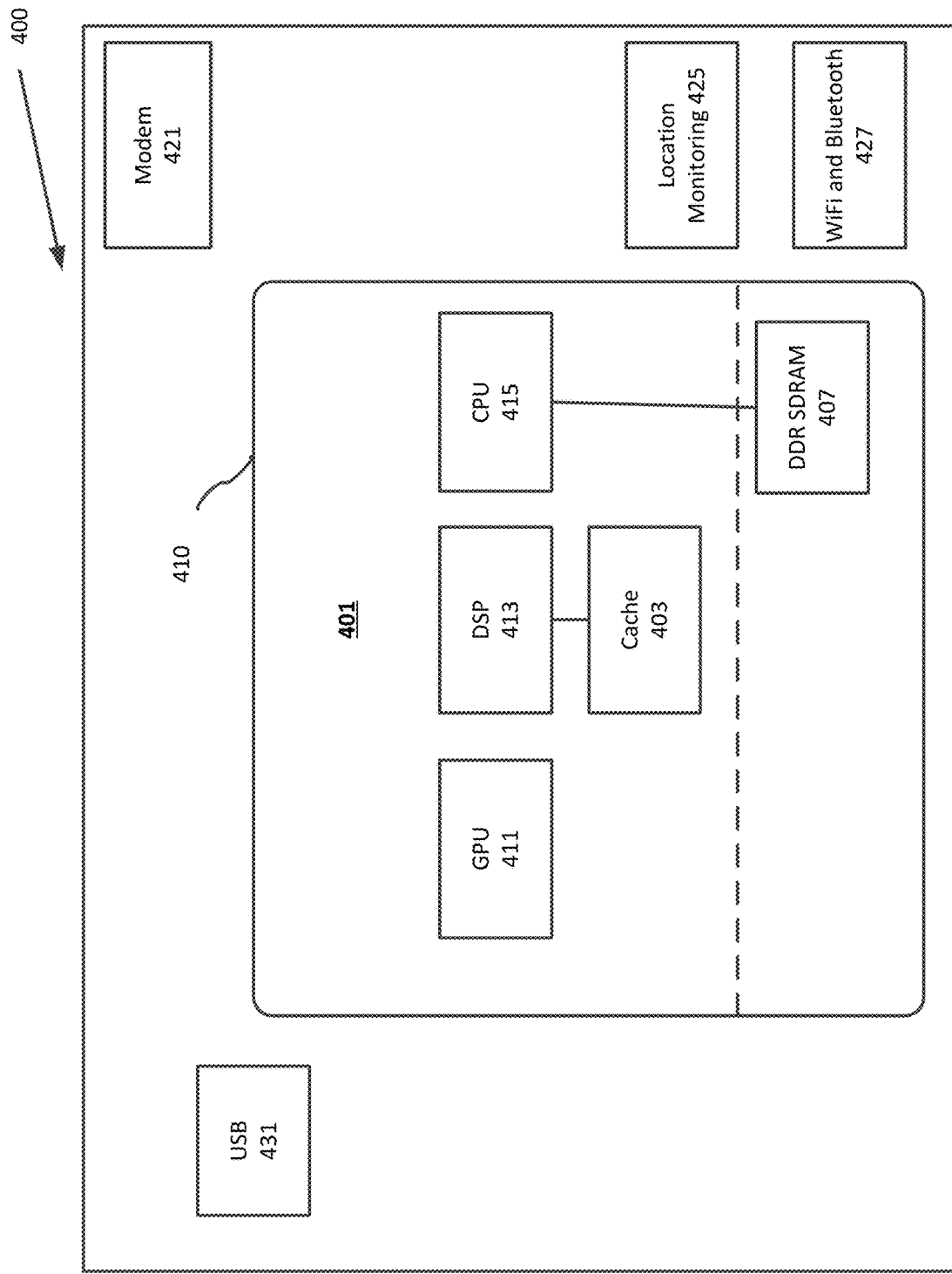
FIG. 4 is a block diagram of a non-limiting example of details of computing hardware, according to certain embodiments.

FIG. 4 is a block diagram of an embedded processing system that may be part of the wearable device in accordance with an exemplary aspect of the disclosure. The embedded processing system 410 provides support for simultaneous sensor inputs, wireless communications, and cellular services 421. The embedded processing system 410 includes processing circuitry 401 that may contain a central processing unit (CPU) 415, as well as a graphics processing unit (GPU) 411 and a digital signal processor (DSP) 413. The CPU 415 may be connected to a memory, which may be any of several types of volatile memory 407, including RAM, SDRAM, DDR SDRAM, to name a few. The DSP 413 and/or the GPU 411 may be a processing core that is specialized for artificial intelligence processing including machine learning operations. The DSP 413 may include one or more dedicated caches 403 in order to perform computer vision functions as well as machine learning functions. The GPU 411 performs graphics processing for an optional 4K resolution display device. The GPU 411, DSP 413, CPU 415, Cache 403, and in some embodiments, a cellular modem 421, may all be contained in a single system-on-chip (SOC) 400. The embedded processing system 410 may also include location service circuitry 425, including GPS and dead reckoning, and connectivity service circuitry 427, including WiFi and Bluetooth. The embedded processing system 410 may include one or more input/output ports, including USB 431 connector(s), such as connectors for USB 2, USB 3, etc.

The above-described hardware description is a non-limiting example of corresponding structure for performing the functionality described herein. For example, the microprocessor of FIG. 4 may be in the form of a microcontroller by including I/O ports, and an optional A/D converter.

In one embodiment, the processing for a Machine Learning model may be performed in an embedded device of the wearable device. FIG. 4 is a block diagram of an embedded microprocessor including processors that may perform artificial intelligence algorithms.

Figure 5:
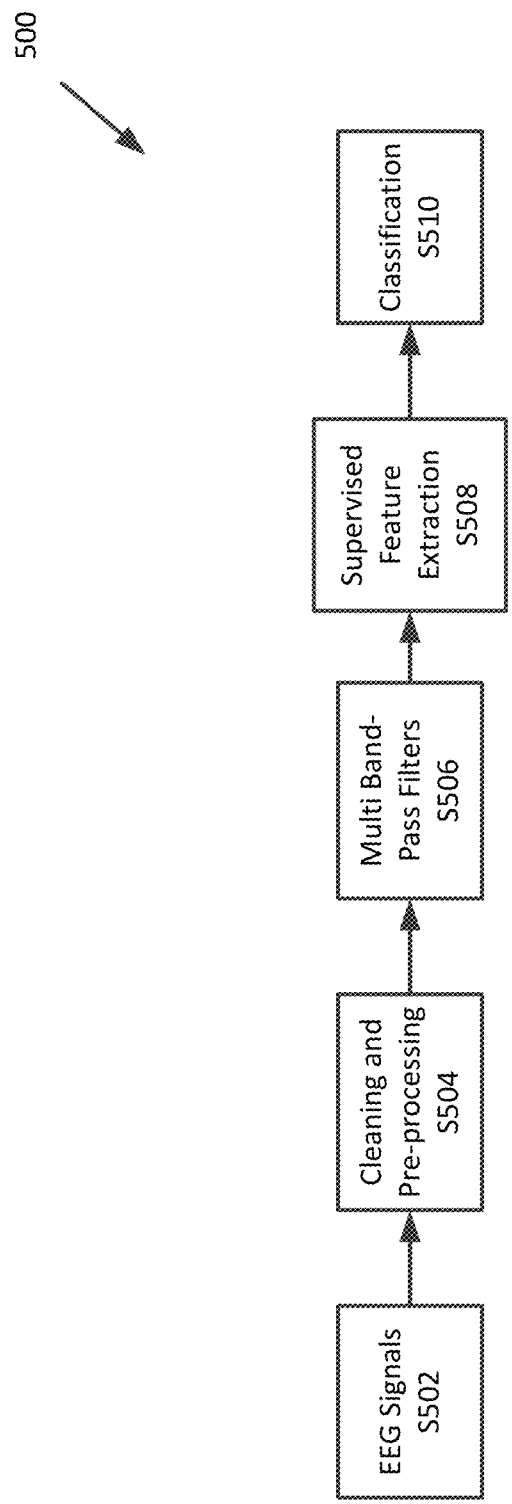
FIG. 5 is block diagram of a conventional machine learning approach.

FIG. 5 shows a conventional Machine Learning approach. The conventional approach 500 may include the following process flow for mental stress classification through EEG signals. In S502, the raw EEG signals are recorded from a device of choice; the raw EEG signals might contain different types of artifacts and noise content. The abnormal EEG rhythms recorded due to muscle movement or the device's electric fluctuation may make it difficult to correctly assess EEG signals.

In S504, pre-processing may be applied to clean the raw EEG signals. The process of pre-processing is itself time consuming because it requires manual operations as well as computation operations. However, pre-processing is important because learning algorithms are sensitive to the types and quality of features.

In order to extract significant features for better discriminating ability, in S506, various types of frequency bands are extracted from the pre-processed EEG signals. In EEG there are five frequency bands that are typically considered for studies: alpha (8-13 Hz), beta (13-30 Hz), theta (4-8 Hz)), delta (1-4 Hz), and gamma (30-50 Hz). In S508, the feature set is extracted from all five of these bands, i.e., power (power spectral density), relative power, asymmetry (differential asymmetry, rational asymmetry), relative power ratio, and coherence. After the process of feature extraction, in S510, these features are classified by a trained machine learning model. The model may contain any machine learning algorithm for classification, i.e., Support Vector Machine (SVM), regression, decision tree, K Nearest Neighbor (KNN), etc.

Steps S504 and S506 are typically the most time-consuming processes due to which performing conventional real-time mental stress assessment is quite impossible. In order to develop a system that can accomplish real-time assessment, the time consuming steps must be reduced. On the other hand, the system should also be capable of performing classification with high accuracy, as well as in the minimum possible time.

Figure 6:
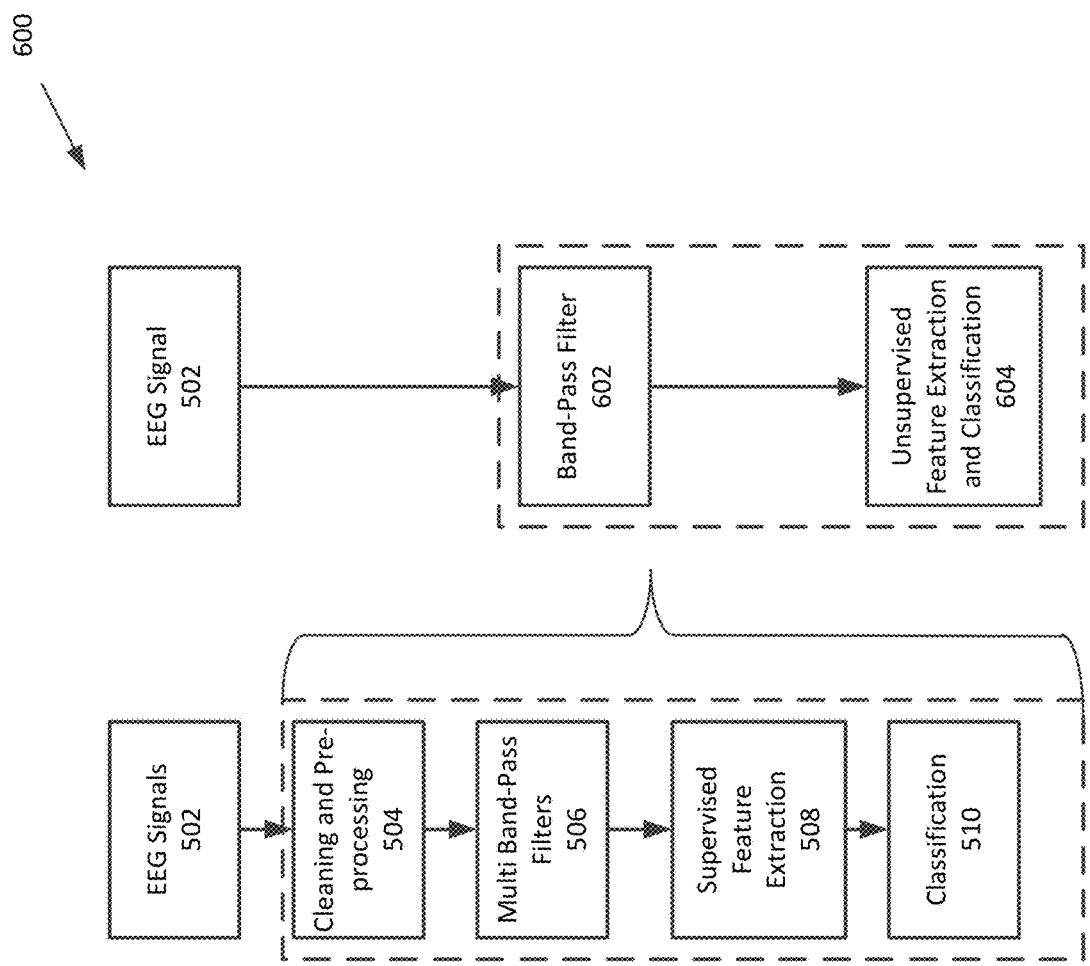
FIG. 6 is flow diagram comparing machine learning approaches.

In order to handle the issues with the existing stress assessment approaches, including raw EEG data, pre-processing, time inefficiency, and classification accuracy, a system and method of real-time mental stress assessment is performed for wearable devices. The method includes three main process blocks as shown in FIG. 6: Raw EEG signal acquisition 502, Frequency Band extraction 602, feature extraction and classification performed in a machine learning model 604. In one or more embodiments, the Frequency Band extraction 602 may be performed using a band-pass filter, which may be included as part of the wearable device 210. In one or more embodiments, the machine learning model 604 may be performed in a controller, such as controller 410, that is part of the harness assembly 216. In one or more embodiments, the machine learning model 604 may be performed in a processor 300 of the wireless device 220.

The system and method has been found to perform real-time stress assessment with high accuracy. The initial process block 502 uses raw EEG signals obtained by an EEG wearable device 210. In order for the system to work in real-time the raw EEG signals may be obtained as short fixed-length windows. These short windows provide high resolution, which helps extract the most significant features associated with stress and non-stress brain conditions. Using short windows enables the participant or patient to not have to wait for long recording periods compared to the conventional approach that uses batch signals of more than 1 min-5 min.

In the conventional approach, due to the large batch size of the signals, the patient has to wait for a specific amount of time to record the signals and perform analysis in order to provide the outcome of the, i.e., stress or non-stress signals. In one or more embodiments, in 502, EEG signals are obtained in short windows of approximately 40 milliseconds in duration, which allows mental stress to be precisely assessed in short intervals. The short windows may be fixed-length windows, preferably of length less than one second, or even less than 50 milliseconds, A minimum length of the windows is approximately 20 milliseconds, to ensure an adequate signal for classification of mental stress assessment.

Band Extraction:

Following the process of obtaining short EEG windows, in 602, each window of EEG signals is fed into a process of frequency band extraction. The raw signals may contain artifacts and device noise. As such, the process of frequency band extraction may be the first level of processing for removing such abnormal rhythms. Because the abnormal rhythms may affect machine learning performance, the resulting machine learning model may over-fit, under-fit, or be very poor at performing classification. Subsequently, in one or more embodiments, frequency band extraction may be enhanced compared to the conventional signal pre-processing.

Conventionally, all five different frequency bands of the EEG signal are separately extracted from the raw EEG signal, which takes an enormous amount of time. In one or more embodiments, instead of extracting the bands separately, the method extracts a combined signal band so that features of the EEG signal can be conserved, and total time consumption can be reduced. In the method, frequency bands from alpha, beta, and theta are obtained, whereas delta and gamma frequency bands are removed by the band-pass filter 602.

LSTM Based Feature Extraction and Classification:

The output from the band extraction module 602 is fed to a classification module 604 for the final classification. The classification module 604 may contain a LSTM machine learning model, which may also perform extraction of significant features. The features extracted by the LSTM are of such a manner that their temporal association is conserved.

Figure 7:
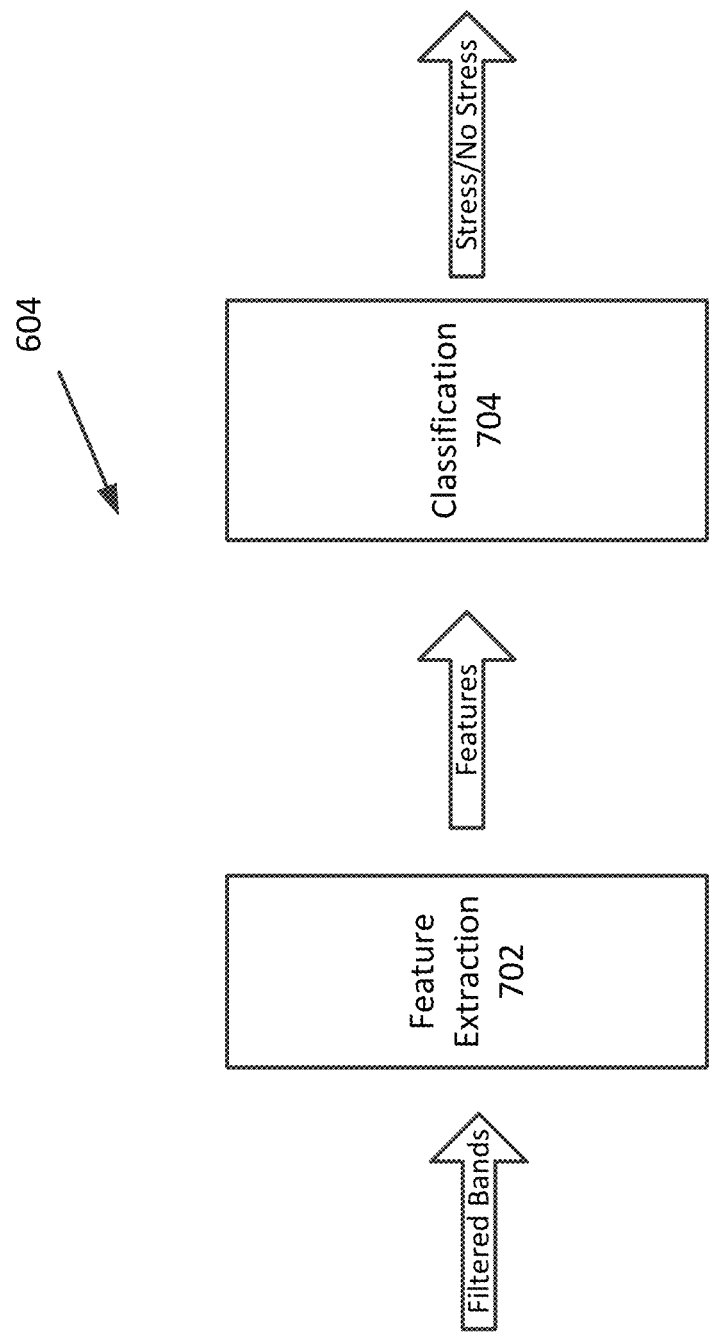
FIG. 7 is a block diagram of the Feature Extraction and Classification of the machine learning, according to certain embodiments.

FIG. 7 is a block diagram of the Feature Extraction and Classification by the machine learning. In an embodiment, a machine learning model may be performed in a controller, e.g., embedded processing system 410, that is part of a wearable device 210. In an embodiment, the machine learning model may be performed in a separate device, such as in the mobile device 220, or in a server computer or cloud service that is accessible via the wireless device connection 230. In an embodiment, the method can include two operations: feature extraction 702 and classification 704. The feature extraction operation 702 takes as input a combined signal of filtered frequency bands and extracts significant features while removing irregularity within the data. The frequency bands include alpha, beta, and theta bands of the EEG signal. The classification operation 704 uses extracted features to classify the signal that the features relate to as being mental stress or not mental stress related.

Figure 8:
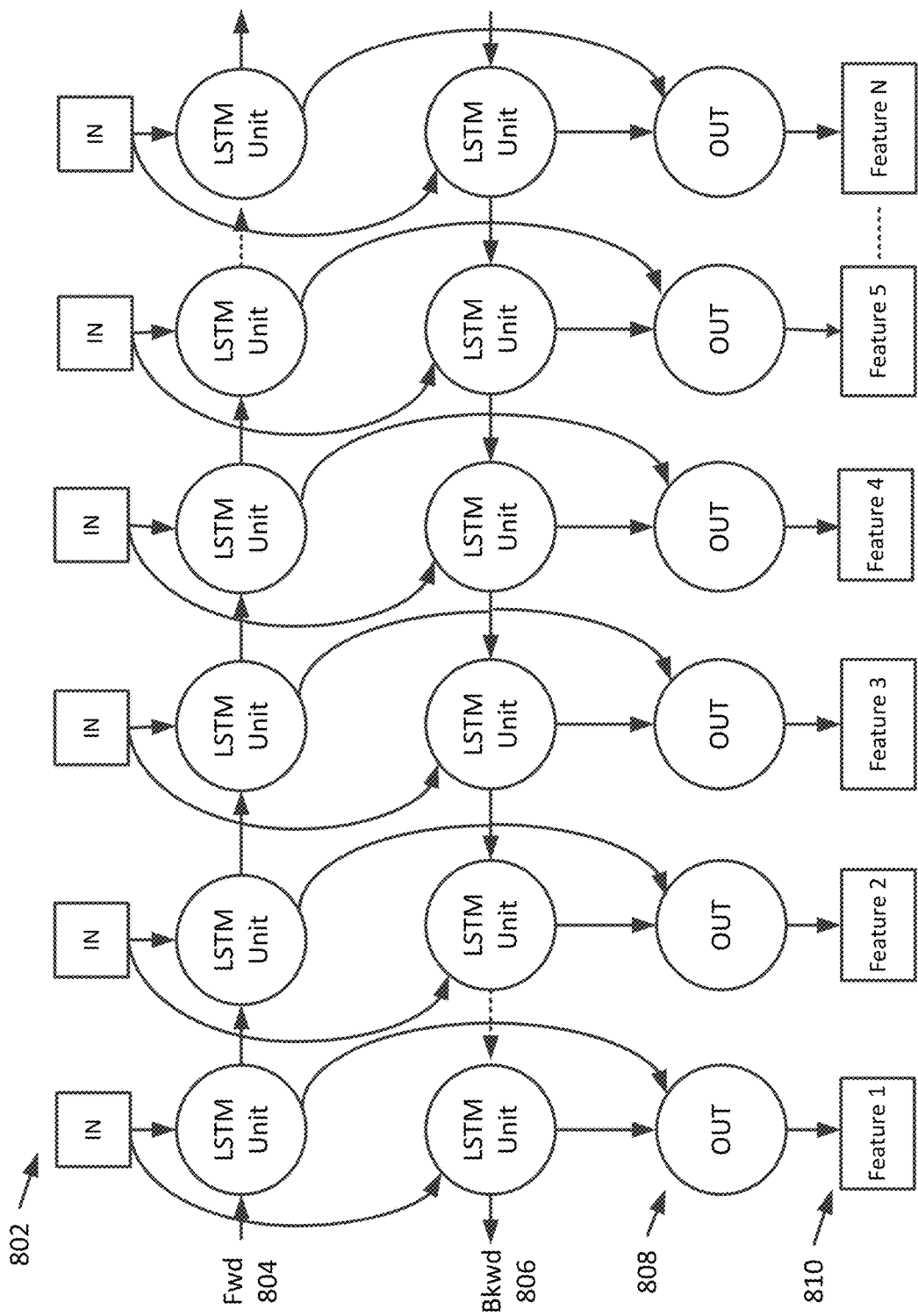
FIG. 8 is a block diagram of a Bidirectional LSTM for unsupervised feature extraction, according to certain embodiments.

FIG. 8 is a block diagram of a Bidirectional LSTM for unsupervised feature extraction. The Bidirectional LSTM 702 performs signal propagation both backward as well as forward in time. The input vector 802 for the BiLSTM is a window of a EEG signal, for example a signal of length 40 milliseconds. The window of the EEG signal propagates both forward through LSTM units 804 and propagates backward through LSTM units 806. The number of LSTM units in the forward and the backward flow is based on the length of the window. Although the LSTM of FIG. 8 shows two Bidirectional layers, the number of layers can be varied. An output layer 808 outputs significant features 810 of the signal. Each of the significant features 810 may be in the form of scores or probabilities (likelihoods). The feature set obtained from the BiLSTM layers are abstract values that are based on the weights determined during the learning phase. A Bidirectional LSTM layer 704 is used for classification of the EEG window 802. The Bidirectional LSTM layer 704 takes as input the extracted features output from the Bidirectional LSTM layer 702. The structure of Bidirectional LSTM layer 704 may be similar to the structure of layer 702. The Bidirectional LSTM 704 propagates forward through LSTM units as well as backward through LSTM units, and includes one or more output neurons that output a classification, as either mental stress or not mental stress related. The output classification may be in the form of a score or probability (likelihood) of the classification.

Figure 9:
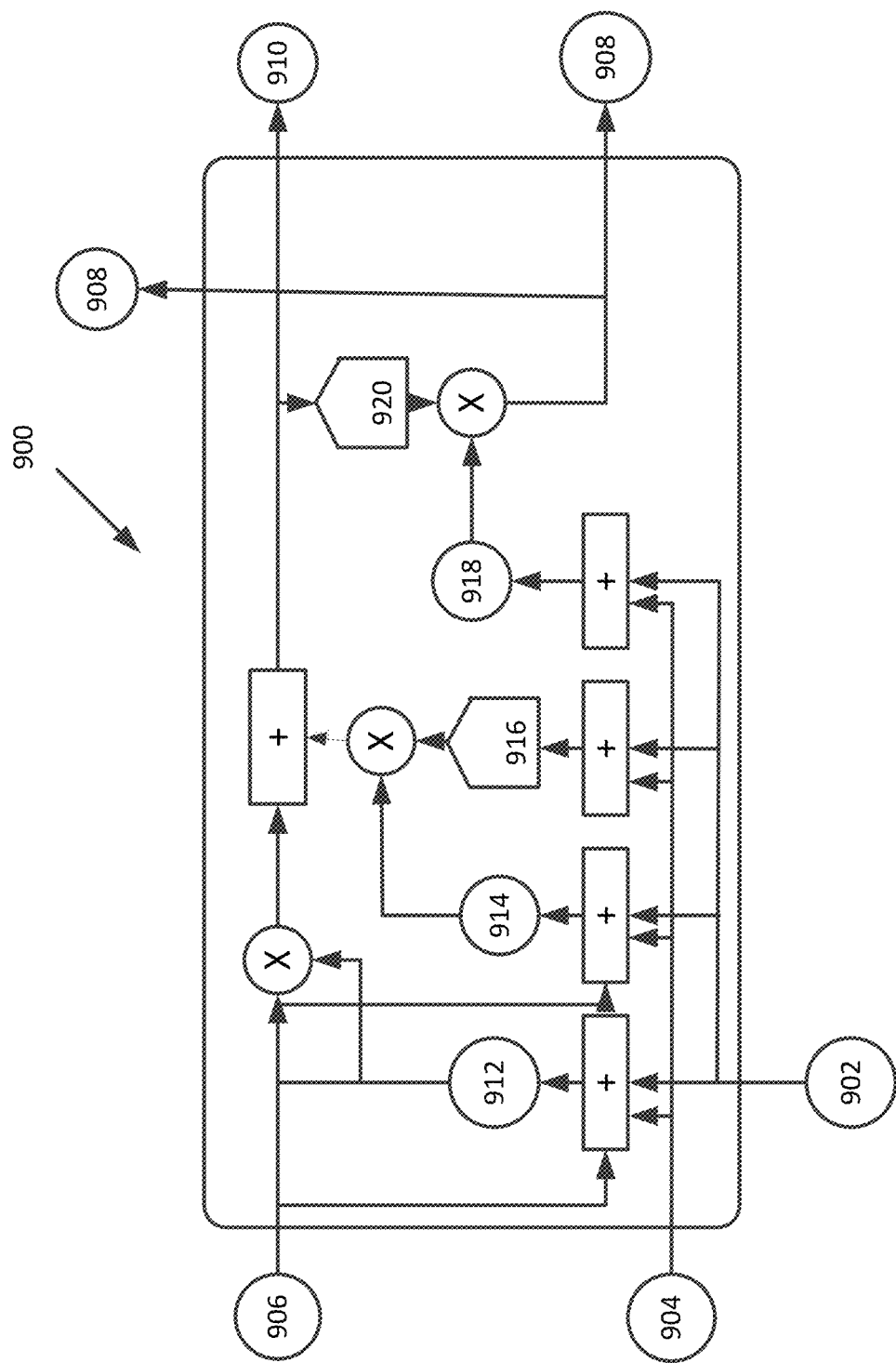
FIG. 9 is a block diagram of gates and cells within a LSTM unit, according to certain embodiments.

FIG. 9 is a block diagram of gates and cells within a LSTM unit. The internal structure of an LSTM unit 900 works on a gate system. In LSTM units, there are gates and a state, i.e., Forget gate, Input gate, Output gate, and Cell state. FIG. 9 shows an LSTM unit 900.

Forget Gate:

Forget gate 912 is responsible for letting information from the previous layer 904 into the current layer. It uses a sigmoid activation function to squish the information into 0-1. A value closer to 0 refers to information to be forgotten, and 1 means to keep the information.

Input Gate:

The data fed into the input gate contains data from a previous unit (output of previous block 904) and referred to as a hidden state, and it is combined with the actual input from the data 902. This combined data is passed through two different activation functions, namely sigmoid 914 and tan h 916. Each function has a different purpose; sigmoid 914 assures which data should be forwarded as it squishes the incoming data into 0-1, whereas tan h 916 regulates the network. The data from the tan h 916 is then checked and multiplied by the output of sigmoid 914 in order to pass the data that has been decided as useful information to be transferred.

Output Gate:

The hidden states are computed with the help of the output gate. The hidden state contains information about the input from the previous cell 904. The hidden state is also used for predictions. First, the previous hidden state 904 and the current input 902 are passed into a sigmoid function 918. Then a newly modified cell state is passed to the tan h function 920. The tan h 920 output is multiplied with the sigmoid 918 output to decide what information the hidden state should carry. The output is the hidden state 908. The new cell state 910 and the new hidden state 908 is then carried over to the next time step.

Cell State:

The new cell state is computed with the help of hidden state 906, input 902, and forget gate 912. First, the hidden state 906 gets point-wise multiplied by the forget vector (output of 912). This can drop values in the cell state if it gets multiplied by values near 0. Then the input gate's output (914, 916) is used to do a point-wise addition that updates the cell state to new values that the neural network finds relevant. That gives a new cell state 910.

Performance

The performance is analyzed by comparing the disclosed LSTM approach and other ML techniques with different features, i.e., coherence, alpha-asymmetry, energy, relative energy, and ratio. The EEG signals are divided into small windows. The features of the windows of EEG signals are used to train the other ML algorithms, i.e., logistic regression (LR), support vector machine (SVM), and decision tree (D-Tree). The maximum accuracy achieved among ML techniques was 57% for LR, 84% for SVM, and 84% for D-Tree.

In a second technique, signal windows are classified with a deep learning approach; for this matter, CNN and the LSTM are used to assess EEG signals. The results obtained by using the CNN and LSTM model outperformed the accuracies achieved by the other ML techniques. The CNN approach was able to classify with an accuracy of 96%, 95% of sensitivity, and 97% specificity whereas, LSTM performed with an accuracy of 98%, sensitivity of 100%, and specificity of 96%.

Another criterion to evaluate the models is computation time. The LSTM model was found to learn a highly compatible model in near real-time assessment, i.e., within 0.12 s. On the other hand, CNN, LR, SVM, and D-Tree consumed 0.65 s, 6.5 s, 6.5 s, and 4.4 s, respectively. Table 2 summarizes the preliminary results for the comparison.

TABLE 2

Comparison of the LSTM method with other
machine learning techniques in terms of
accuracy, sensitivity, specificity, and computation time.

| Performance/Techniques | LR | SVM | D-Tree | CNN | LSTM |
|---|---|---|---|---|---|
| Accuracy | 57% | 84% | 84% | 96% | 98% |
| Sensitivity | 64% | 78% | 91% | 95% | 100% |
| Specificity | 48% | 90% | 71% | 97% | 96% |
| Computation Time | 6.5 s | 6.87 s | 4.41 s | 0.65 s | 0.12 s |

Referring again to FIG. 1, the figure shows a conceptual flow of the disclosed methodology. In general, a feature of the method is that it performs mental stress assessment in real-time using raw EEG signals with minimum complexity. This makes it a perfect approach for wearable devices. Following are the features of the method:

The method can extract the features automatically in an unsupervised manner.

The method enables conserving the temporal information within the EEG signals and extracts significant hidden information between these temporal associations.

The method also relies on the band extraction module that provides a specific range of bands to the LSTM model for classification.

The method performs the required classification in a minimum amount of time, making it compatible with real-time stress assessment. The method is fast and computationally efficient in providing the assessment; hence it is very much compatible with wearable devices. Table 3 below gives a comparison of the method with the existing methods.

TABLE 3

Comparison of the LSTM method with
other machine learning methods

| Aspect | Existing Methods | Proposed Method |
|---|---|---|
| Accuracy | Low | High |
| Raw EEG data | Not possible as it results in low accuracy | Suitable for raw EEG data and results in high accuracy |
| Efficiency | Low | High |
| Suitable for real-time applications | No | Yes |
| Generic | No | Yes |

Numerous modifications and variations of the present disclosure are possible in light of the above teachings. It is therefore to be understood that within the scope of the appended claims, the invention may be practiced otherwise than as specifically described herein.

The invention claimed is:

1. A wearable stress assessment system, comprising:
a wearable device having:
  a plurality of EEG sensors to detect and acquire an EEG signal, and a plurality of semicircular bands configured to loop over the scalp of an individual wearing the wearable device and support the plurality of EEG sensors,
  a harness connected to the plurality of EEG sensors, a plurality of first temperature probes and one or more second temperature probes, wherein each of the first temperature probes is proximal to an EEG sensor, wherein the first temperature probes are connected to the harness and are configured to measure a surface temperature of skin of the individual wearing the wearable device, and wherein the one or more second temperature probes are mounted on the harness and are configured to measure a second temperature without contacting the skin of the individual wearing the wearable device;
  a bandpass filter to obtain alpha, beta, and theta frequency bands from the EEG signal, and
  a wireless device connection to wirelessly transmit information from the wearable device, the information including the EEG signal and the alpha, beta, and theta frequency bands; and
a mobile device including:
  a communication device for receiving the wirelessly transmitted information,
  a microcontroller for
    extracting features from the alpha, beta, and theta frequency bands obtained from the bandpass filter with processing circuitry having a machine learning model, and
    classifying the features from the alpha, beta, and theta frequency bands to obtain a classification result of mental stress or no mental stress,
    wherein the machine learning model has a first bidirectional long short term memory (LSTM) layer and a second bidirectional long short term memory layer; and
  wherein the processing circuitry of the microcontroller is configured to perform the extracting with the first bidirectional LSTM layer of the machine learning model and perform the classifying with the second bidirectional LSTM layer of the machine learning model to obtain the classification result of mental stress or no mental stress; and
  a display device displaying the EEG signal and the classification result.

* * * * *